(12) United States Patent
Popovic et al.

(10) Patent No.: US 8,934,003 B2
(45) Date of Patent: Jan. 13, 2015

(54) UNCALIBRATED VISUAL SERVOING USING REAL-TIME VELOCITY OPTIMIZATION

(75) Inventors: Aleksandra Popovic, New York, NY (US); Paul Thienphrapa, Baltimore, MD (US)

(73) Assignee: Koninklijkle Philips N.V., Eindhoven (NL)

( * ) Notice: Subject to any disclaimer, the term of this patent is extended or adjusted under 35 U.S.C. 154(b) by 351 days.

(21) Appl. No.: 13/519,383

(22) PCT Filed: Nov. 17, 2010

(86) PCT No.: PCT/IB2010/055245
§ 371 (c)(1),
(2), (4) Date: Jul. 11, 2012

(87) PCT Pub. No.: WO2011/083374
PCT Pub. Date: Jul. 14, 2011

(65) Prior Publication Data
US 2012/0307027 A1    Dec. 6, 2012

Related U.S. Application Data

(60) Provisional application No. 61/293,222, filed on Jan. 8, 2010.

(51) Int. Cl.
*H04N 7/18* (2006.01)
*A61B 19/00* (2006.01)

(52) U.S. Cl.
CPC ......... *A61B 19/2203* (2013.01); *A61B 19/5212* (2013.01); *A61B 19/5244* (2013.01)
USPC ................................ 348/65; 348/61; 348/169

(58) Field of Classification Search
USPC ............. 348/65, 61, 135, 141, 169–172, 159, 348/46; 901/46, 30, 32, 15; 73/514.01, 491
IPC ..................................... H04N 13/02,7/18, 5/225
See application file for complete search history.

(56) References Cited

U.S. PATENT DOCUMENTS

| | | | |
|---|---|---|---|
| 6,278,906 | B1 | 8/2001 | Piepmeier et al. |
| 2003/0065310 | A1 | 4/2003 | Wang et al. |

(Continued)

FOREIGN PATENT DOCUMENTS

| | | | |
|---|---|---|---|
| CN | 1216454 A | 5/1999 | |
| CN | 1843710 A | 10/2006 | |

(Continued)

OTHER PUBLICATIONS

M. Bonkovic, "Nonlinear Optimization Methods for Uncalibrated Robot Visual Servoing", Department for Robotics and Intelligent Systems, University of Split, Rudera Boskovica bb, Croatia.

(Continued)

*Primary Examiner* — Sherrie Hsia

(57) ABSTRACT

A robotic control method for a camera (30) having an optical view and a robot (40) having an end-effector (42) and one or more joints (41) for maneuvering end-effector (42). The robotic control method involves an acquisition of a digital video frame (32) illustrating an image as optically viewed by the camera (30), and an execution of a visual servoing for controlling a pose of end-effector (42) relative to an image feature within the digital video frame (32). The visual servoing involves an identification of a tracking vector (vtrk) within an image coordinate system (80) of the digital video frame (32) extending from a tracking point (TR) to a target point (TG) associated with the image feature, a mapping of the tracking vector within a configuration space (100) constructed from a robotic coordinate system (90) associated with the end-effector (42), and a derivation of a pose of the end-effector (42) within the robotic coordinate system (90) from the mapping of the tracking vector (vtrk) within the configuration space (100).

20 Claims, 10 Drawing Sheets

(56) References Cited

U.S. PATENT DOCUMENTS

| | | | |
|---|---|---|---|
| 2007/0142823 A1 | 6/2007 | Prisco et al. | |
| 2011/0205338 A1* | 8/2011 | Choi et al. | 348/46 |
| 2012/0044355 A1* | 2/2012 | Jamtgaard et al. | 348/159 |

FOREIGN PATENT DOCUMENTS

| | | |
|---|---|---|
| EP | 1769769 | 4/2007 |
| EP | 2047805 | 4/2009 |
| WO | WO2009045827 | 4/2009 |

OTHER PUBLICATIONS

M. Hao, et al., "Model-Free Uncalibrated Visual Servoing Using Recursive Least Squares", Journal of Computers, vol. 3, No. 11, Nov. 2002, pp. 42-50.

Shunsuke Namba et al, "Endoscopic Instrument Interface with Touch Panel Using Visual Servoing", Department of Mechanical Science and Bioengineering, Graduate School of Engineering Science, Osaka University. 46 (6), pp. 595-605, 2008.

Liu Hongding et al, "Recognition and Servo Tracking of Moving Target Based on Image Features", Chinese Journal of Scientif Instrument, vol. 29, No. 3, pp. 644-648.

* cited by examiner

UNCALIBRATED VISUAL SERVOING USING REAL-TIME VELOCITY OPTIMIZATION

The present invention generally relates to a visual servoing of a robot during a robotic procedure. The present invention specifically relates to a visual servoing of an endoscopic robot during a minimally invasive surgery.

Generally, a minimally invasive surgery utilizes an endoscope, which is a long, flexible or rigid tube having an imaging capability. Upon insertion into a body through a natural orifice or a small incision, the endoscope provides an image of the region of interest that may be viewed through an eyepiece or on a screen as a surgeon performs the operation.

Visual servoing is a robot control method using a visual input (images) to set robot movement parameters. This method is used for robotic following of targets, for autonomous robots, etc. In surgical robotics, visual servoing is used in the control loops with medical images to guide robots towards some specific anatomical (e.g., organs) or surgical targets (e.g., instruments). A standard imaging modality for visual servoing in this domain is a rigid endoscope. The camera feed of the endoscope is connected to the robot control loop providing steering information.

To close the control loop of visual servoing, a mathematical transformation between image coordinates and robotic joint space has to be established (referred to as Image Jacobian). The entire process is referred to as the system calibration and requires various steps such as camera calibration and robot calibration. Furthermore, to provide full calibration, depth between the camera and the organ/object under consideration needs to be measured either from images or from using special sensors.

More particularly, camera calibration is a process to establish inherent camera parameters such as, for example, the optical center of the image, focal lengths in both directions and the pixel size. This is usually done preoperatively and involves acquisition of several images of a calibration object (usually a chessboard-like object) and computation of parameters from those images. If some of the parameters are changed during the surgery (e.g., camera focus is changed), then the camera calibration needs to be repeated.

Robot calibration is a process of establishing the mathematical relation between the joint space of the robot and the end-effector, an endoscope in this domain. This process is a straightforward procedure, well established in practice. However, it usually requires a technical expert to perform the calibration. If the user/surgeon moves an endoscope relative to the robot, then the robot calibration needs to be repeated.

Different approaches for solving visual servoing in medical robotics, especially endoscopic surgery, have been proposed, but all of these approaches rely on Image Jacobian, which may experience numerous drawbacks as known in the art.

The present invention provides a visual servoing technique that does not rely on Image Jacobian or depth perception from endoscopy images. More particularly, the visual servoing technique of the present invention involves a robot holding an endoscope that eliminates the need for calibrating the endoscope or for obtaining relative position of the endoscope image to the robot. The visual servoing technique of the present invention further allows a robotic system to be used with a standard endoscope without any adjustments to the hardware and without additional procedures in the surgery workflow. The visual servoing of the present invention further allows an intra-operative change of endoscopes (e.g., forward looking to oblique or vice versa).

One form of the present invention is a robotic system employing a camera (e.g., an endoscope), a robot and a robot controller. The camera has an optical view (e.g., forward or oblique) for acquiring a digital video frame illustrating an image. The robot includes an end-effector and one or more joints for maneuvering the end-effector. The robot controller includes a visual servo for controlling a pose of the end-effector relative to an image feature within the digital video frame. To this end, the visual servo identifies a tracking vector within an image coordinate system of the digital video frame extending from a tracking point to a target point associated with the image feature, maps the tracking vector within a configuration space constructed from a robotic coordinate system associated with the end-effector, and derives a pose of the end-effector within the robotic coordinate system from the mapping of the tracking vector within the configuration space.

A second form of the present invention is a robotic control method including a camera having an optical view and a robot having an end-effector and one or more joints for maneuvering the end-effector. The robotic control method involves an acquisition of a digital video frame illustrating an image as optically viewed by the camera, and an execution of a visual servoing for controlling a pose of the end-effector relative to an image feature within the digital video frame. The visual servoing involves an identification of a tracking vector within an image coordinate system of the digital video frame extending from a tracking point to a target point associated with the image feature, a mapping of the tracking vector within a configuration space constructed from a robotic coordinate system associated with the end-effector, and a derivation of a pose of the end-effector within the robotic coordinate system from the mapping of the tracking vector within the configuration space.

Figure 1:
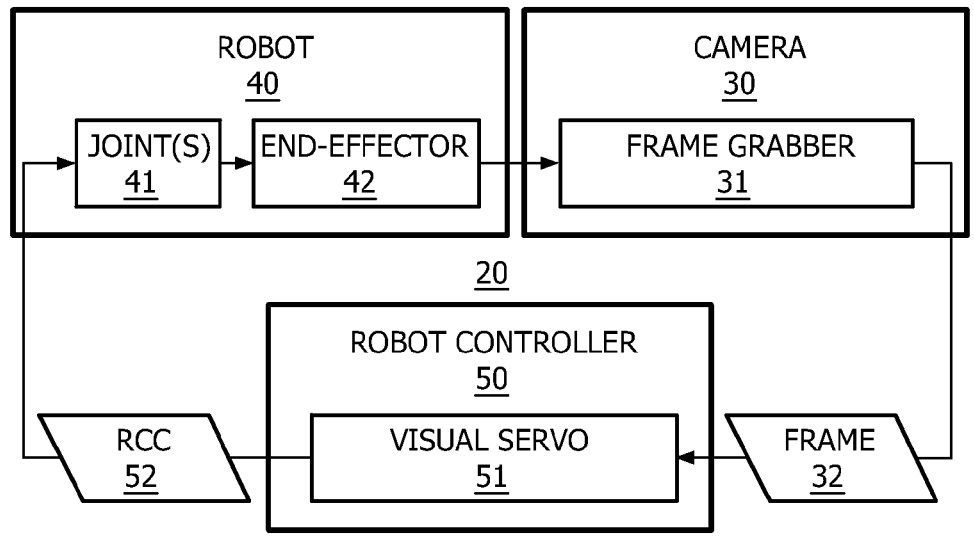
FIG. 1 illustrates an exemplary embodiment of a robotic system in accordance with the present invention.

As shown in FIG. 1, a robotic system 20 employs a camera 30, a robot 40 and a robot controller 50 for any robotic procedure involving automatic motion capability of robot 40. Examples of such robotic procedures include, but are not limited to, medical procedures, assembly line procedures and procedures involving mobile robots. In particular, robotic system 20 may be utilized for medical procedures including, but are not limited to, minimally invasive cardiac surgery (e.g., coronary artery bypass grafting or mitral valve replacement), minimally invasive abdominal surgery (laparoscopy) (e.g., prostatectomy or cholecystectomy), and natural orifice translumenal endoscopic surgery.

Camera 30 may be any type of camera having a forward optical view or an oblique optical view, and employing a frame grabber 31 of any type that is capable of acquiring a sequence of two-dimensional digital video frames 32 at a predefined frame rate (e.g., 30 frames per second). In one exemplary embodiment, camera 30 is an endoscope broadly defined herein as any device structurally configured for imaging an anatomical region of a body (e.g., human or animal) via an imaging device (e.g., fiber optics, lenses, miniaturized CCD based imaging systems, etc) having a forward optical view or an oblique optical view and employing a digital frame grabber capable of providing each digital video frame 32 to robot controller 50. Examples of the endoscope include, but are not limited to, any type of imaging scope (e.g., a bronchoscope, a colonoscope, a laparoscope, an arthroscope, etc.) and any device similar to a scope that is equipped with an image system (e.g., an imaging cannula).

Robot 40 is broadly defined herein as any robotic device structurally configured with motorized control of one or more joints 41 for maneuvering an end-effector 42 of robot 40 as desired for the particular robotic procedure. In practice, robot 40 may have a minimum of four (4) degrees-of-freedom, preferably six (6) or seven (7) degrees-of-freedom.

A pose of end-effector 42 is a position and an orientation of end-effector 42 within a coordinate system of robot 40, and any given pose of end-effector 42 dictates a pose of the optical view of camera 40 within the coordinate system of robot 40. As such, camera 30 may be mounted to end-effector 42 (e.g., an endoscope mounted on robot 40 for providing a view of an anatomical region of a body during a medical procedure).

For embodiments of robot 40 involving camera 30 having a forward optical view, robot 40 may allow for any provisory orientation of camera 30 (e.g., an intra-operative manual rotation of camera 30 about a longitudinal axis of camera 30). For embodiments of robot 40 involving camera 30 having an oblique optical view, robot 40 may have a specific joint for rotating camera 30 about a longitudinal axis of camera 30.

Robot controller 50 is broadly defined herein as any controller structurally configured to provide one or more robot control commands ("RCC") 52 to robot 40 for controlling a pose of end-effector 42 as desired for a particular robotic procedure by commanding definitive movements of each robotic joint(s) 41 as needed to achieve the desired pose of end-effector 42.

For example, with camera 30 being an endoscope mounted onto end-effector 42, robot control command(s) 52 may move one or more robotic joint(s) 41 as needed for facilitating a tracking of an instrument tip of a surgical tool by the endoscope to provide a consistent view of the tip for a surgeon, or for steering the endoscope toward a specific anatomical feature such as blood vessels in cardiac surgery, or for coinciding physiological movement of the endoscope with an organ to provide a stable image of an anatomical view of the organ.

For robotic tracking of a feature of an image within digital video frames 32, robot controller 50 includes a visual servo 51 for controlling the pose of end-effector 42 relative to a feature of an image within each digital video frame 32. Specifically, visual servo 51 implements a static or dynamic robotic tracking of a defined target point (e.g., one or more pixels) of a particular image feature within digital video frames 32 by an execution of an adaptive algorithm that automatically identifies a tracking vector extending from a tracking point (e.g., one or more pixels) to the target point within digital video frames 32. Additionally, the adaptive algorithm updates the tracking vector as needed for each digital video frame 32 or at any specified frame-rate of digital video frames 32.

Figure 2:
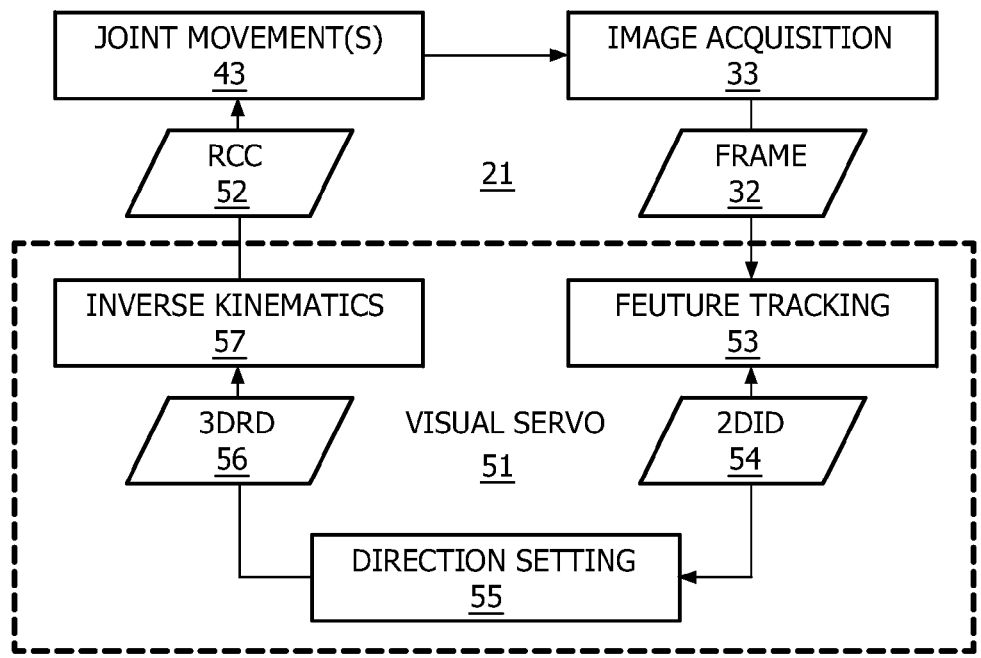
FIG. 2 illustrates an exemplary embodiment of a robot control loop in accordance with the present invention.

To this end, as shown in FIG. 2, visual servo 51 implements a feature tracking process 53, a direction setting process 55 and an inverse kinematics process 57 in a closed robot control loop 21 with an image acquisition 33 implemented by frame grabber 31 and controlled movement(s) 43 of robotic joint(s) 41. In practice, processes 53, 55 and 57 may be implemented by modules of visual servo 51 (not shown) that are embodied by hardware, software and/or firmware installed on any platform (e.g., a general computer, ASIC board, etc.)

Referring to FIG. 2, feature tracking process 53 involves an individual processing of each digital video frame 32 to identify the target point of a particular image feature within digital video frames 32 as known in the art. For example, FIGS. 3-6 show four (4) digital video frames 32 of a target point TG of a particular image feature symbolized by a black X. In this example of FIGS. 3-6, the particular feature may be an instrument tip of a surgical tool with camera 30 being an endoscope for providing a consistent view of the tip for a surgeon, or the particular feature may be a definitive portion of a specific anatomical feature such as blood vessels or an organ.

Referring again to FIG. 2, feature tracking 53 generates two-dimensional image data ("2DID") 54 indicating the tracked movements of the target point within each digital video frame 32, and direction setting process 55 in turn processes 2D data 54 to identify a tracking vector (e.g., tracking direction and a tracking speed) extending from a tracking point to the target point for each digital video frame 32. The identification of the tracking vector sets a fixed tracking direction extending from the tracking point to the target point, and sets a tracking speed that may also be fixed or alternatively adjusted to optimize a tracking of the target point. For each digital video frame 32 having a tracking vector of any magnitude or of a minimum magnitude, direction setting process 55 generates three-dimensional robot data ("3DRD") 56 indicating the desired pose of end-effector 42 of robot 40 relative to the image feature within digital video frames 32. Inverse kinematics process 57 processes 3D data 56 as known in the art for generating one or more robot control command(s) 52 as needed for the appropriate joint movement(s) 43 of robotic joint(s) 41 to thereby achieve the desired pose of end-effector 42 relative to the image feature within the digital video frame 32.

Figure 3:
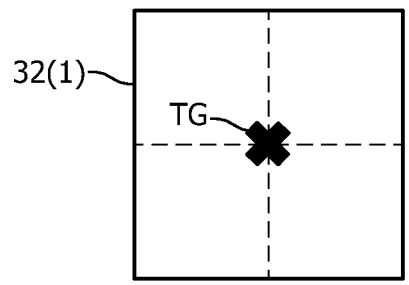
FIGS. 3-6 illustrate an exemplary sequence of digital video frames in accordance with the robot control loop shown in FIG. 2.
Figure 4:
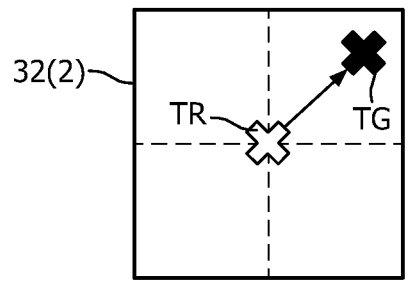

For example, FIGS. 3-6 illustrate an identification of a tracking vector extending from a tracking point TR symbolized by a white X to target point TG. Specifically, FIG. 3 shows a digital video frame 32(1) having the target point TG initialized at the tracking point TR. As the target point TG moves away tracking point TR within digital video frame 32(2) as shown in FIG. 4, direction setting process 55 identifies a tracking vector symbolized by the arrow pointing from tracking point TR to the target point TG. From the identification of the tracking vector, direction setting process 55 sets the tracking direction for moving tracking point TR within digital video frame 32(2) in a direction of target point TG for digital video frame 32(3) and utilizes the tracking direction and the tracking speed of tracking vector to determine a desired pose of end-effector 42 of robot 40 relative to the image feature within the digital video frame 32(2). In turn, inverse kinematics process 57 generates robot control command(s) 52 as needed for the appropriate joint movement(s) 43 of robotic joint(s) 41 to thereby achieve the desired pose of end-effector 42 relative to the image feature within the digital video frame 32(2).

Figure 5:
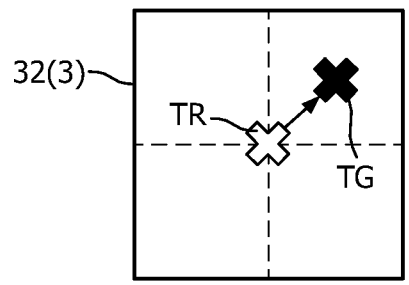

As shown in FIG. 5, digital video frame 32(3) illustrates tracking point TR being moved in the direction of target point TG, but target point TG is still displaced from tracking point TR. Direction setting process 55 again identifies a tracking vector symbolized by the arrow pointing from tracking point TR to the target point TG. From the identification of the tracking vector, direction setting process 55 sets a tracking direction for moving tracking point TR within digital video frame 32(4) in a direction of target point TG for digital video frame 32(5) (not shown) and utilizes the tracking direction and the tracking speed of the tracking vector to determine a desired pose of end-effector 42 relative to the image feature within the digital video frame 32(3). Again, inverse kinematics process 57 generates robot control command(s) 52 as needed for the appropriate joint movement(s) 43 of robotic joint(s) 41 to thereby achieve the desired pose of end-effector 42 of robot 40 relative to the image feature within the digital video frame 32(4).

Figure 6:
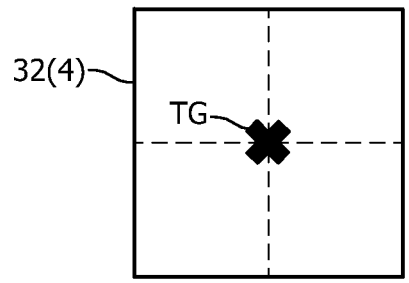

As shown in FIG. 6, digital video frame 32(4) illustrates tracking point TR and target point TG once again coincide. As such, the tracking vector for digital video frame 32(4) is zero and robot controller 50 will maintain robotic joint(s) 41 in a fixed state until such time subsequent digital video frames 32 indicate a non-zero tracking vector or a tracking vector of a minimum magnitude between tracking point TR and target point TG.

The description of FIGS. 1-6 herein facilitates a general understanding of visual servo 51. The following description of an exemplary embodiment of visual servo 51 as shown in FIGS. 8-16 facilitates a more detailed understanding of visual servo 51. In particular for the visual servoing method of FIGS. 15 and 16, the tracking velocity is adjusted as needed in each video frame or at any specified frame-rate until the best tracking velocity is locked.

Figure 7:
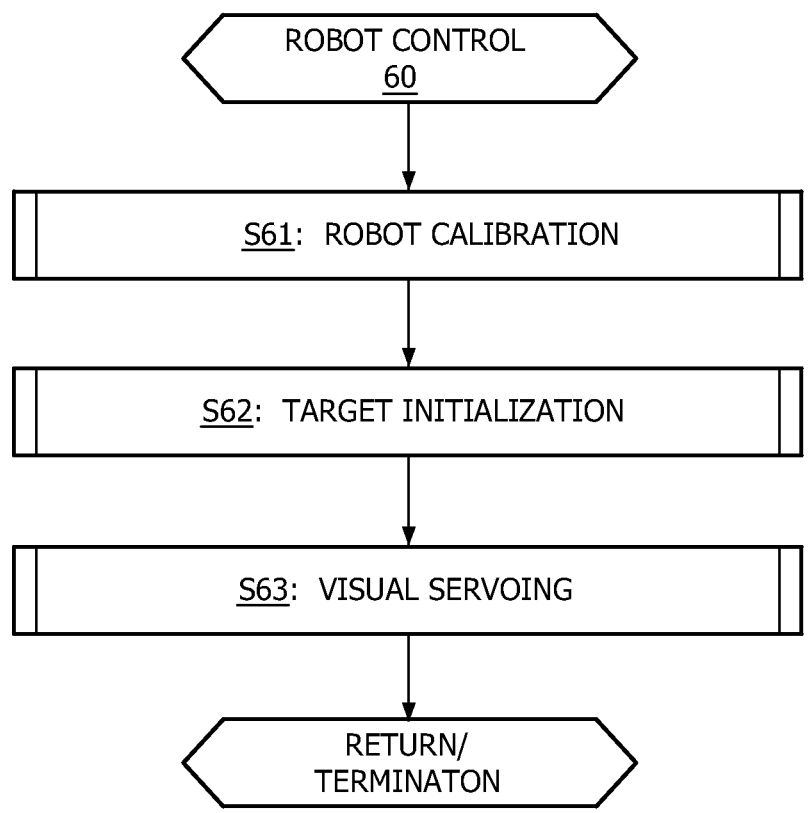
FIG. 7 illustrates a flowchart representative of an exemplary embodiment of a robot control method in accordance with the present invention.

FIG. 7 illustrates a flowchart 60 representative of a robot control method executed by robotic system 20 (FIG. 1) on behalf of visual servo 51. Specifically, flowchart 60 includes robot calibration stage S61 and a target initialization stage S62 as pre-requisites for a visual servoing stage S63. In practice, upon an initial implementation of stage S61, only stages S62 and S63 may need to be executed for new image features to be tracked as would be appreciated by those skilled in the art.

Stage S61 encompasses a robot calibration of robot 40 as known in the art involving an establishment of a mathematical relation between a joint space of robot 40 and end-effector 42.

Stage 62 encompasses a target initialization of a particular feature of an image within digital video frames 32 as known in the art. In one exemplary embodiment of stage S62, vertical motion (insertion) of camera 30 within a particular environment is a parameter settable by a user of system 20 and therefore is beyond automatic control by visual servo 51. As such, after insertion of camera 30 within the environment, automatic control of robot 40 by visual servo 51 may be performed in two (2) end-effector 42 degrees of freedom including a theta angle θ and a phi angle ϕ for defining a two-dimensional spherical cap for robot 40. This may involve an establishment of a virtual remote-center-of-rotation ("RCM") for robot 40 upon an insertion of camera 30 within the environment whereby the virtual RCM fixes movements of robot 40 around a specified pivot point that defines a spherical conic workspace for robot 40 (e.g., an insertion point of an endoscope through a small incision in a patient's body during a minimally invasive surgical procedure). The spherical conic workspace is transformed into a two-dimensional spherical cap based on the theta angle θ and the phi ϕ angle as would be appreciated by one skilled in the art.

For RCM embodiments of robot controller 50 whereby camera 30 is an endoscope, the RCM point relative to the endoscope may be defined by (1) a utilization of a marker arranged along a shaft of the endoscope at a fixed distance from a tip the endoscope; (2) a user specification via a computer program of a distance between the RCM point and a tip of the endoscope; (3) a positioning of the tip of the endoscope scope at the desired insertion point followed by setting of the insertion point as the RCM and an insertion of the endoscope to the desired depth; or (4) a utilization of a predetermined point in space relative to robot 40 and a positioning of robot 40 whereby the predetermined point coincides with the desired insertion point.

In practice, RCM-based motion of robot 40 will be the typical mode of operation implemented by robot controller 50 for the visual servoing of stage S63 of flowchart 60. Alternatively, robot controller 50 may implement an initial positioning of camera 40 for the visual servoing of stage S63 that defines the spherical conic workspace for camera 40. For any mode of operation (RCM or not), stage S63 encompasses a visual servoing involving feature tracking process 53 and inverse kinematics process 57 as previously described herein in connection with the description of FIG. 2, and involves an exemplary embodiment of direction process setting 55 as shown in FIGS. 8-16.

Figure 8:
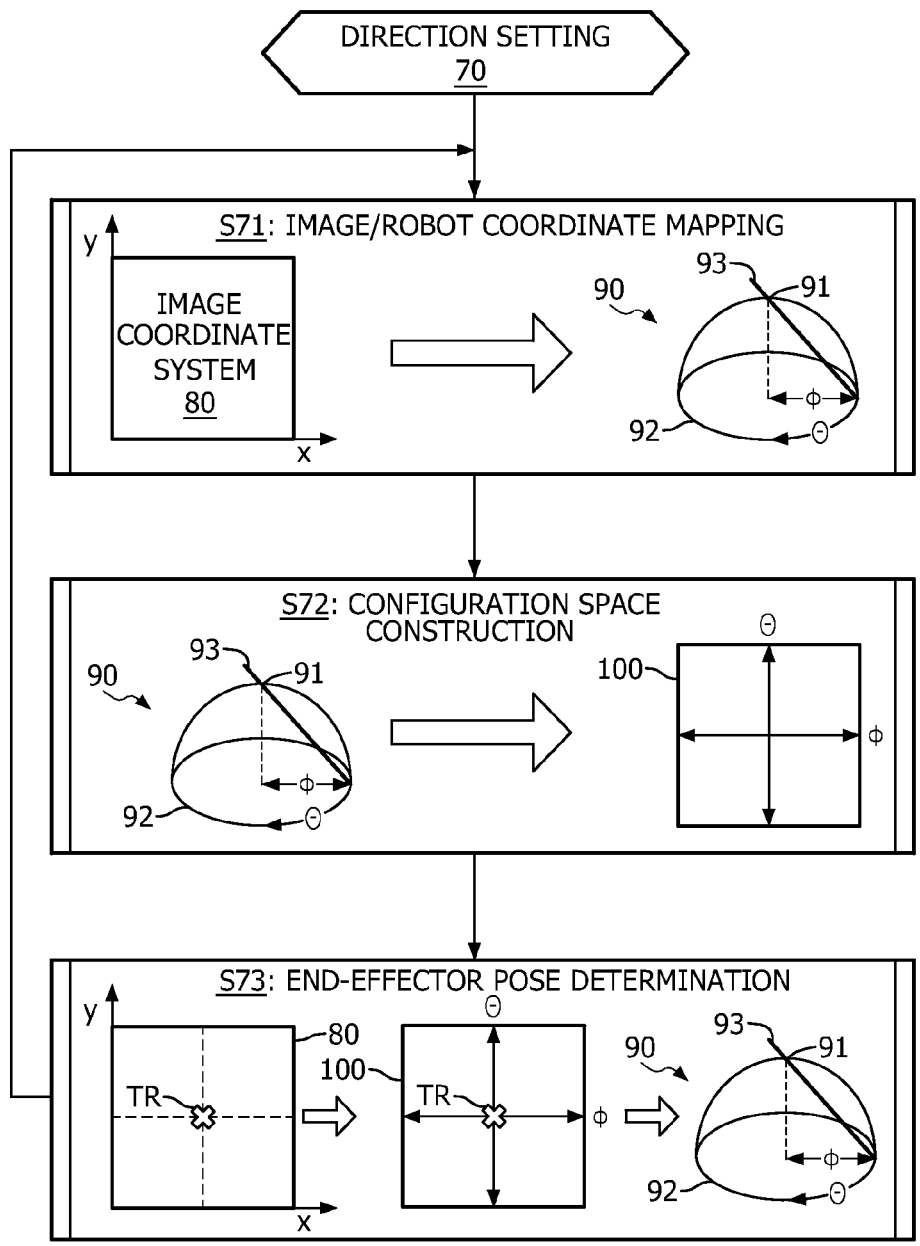
FIG. 8 illustrates a flowchart representative of an exemplary embodiment of a direction setting method in accordance with the present invention.

Specifically, FIG. 8 illustrates a flowchart 70 representative of a direction setting method of the present invention. To facilitate an understanding of flowchart 70, end-effector 42 is represented by an endoscopic end-effector 93. In one embodiment, endoscopic end-effector 93 is an endoscope having a proximal end coupled to robot 40 by any means known in the art.

Referring to FIG. 8, stage S71 of flowchart 70 encompasses a mapping of a two-dimensional image coordinate system 80 of each digital video frame 32 to a three-dimensional, two degrees-of-freedom robot coordinate system 90 of robot 40. In one embodiment of as shown in stage S71, image coordinate system 80 has an x axis and a y axis, and robot coordinate system 90 is a spherical cap having an axis symbolized by a dashed line extending from a pivot point 91 (e.g., a virtual RCM) to a two-dimensional plane 92 outlined by a full rotation of a endoscopic end-effector 93 about pivot point 91. In practice where a distance between pivot point 91 and a distal tip of endoscopic end-effector 93 is known, the theta angle θ explicitly quantifies the degree of rotation of the distal tip of endoscopic end-effector 93 about the axis of the spherical cap relative to an origin point along a periphery of plane 92, and the phi angle ϕ explicitly quantifies the degree of separation between the distal tip of endoscopic end-effector 93 from the axis of the spherical cap. Alternatively, in practice where the distance between pivot point 91 and a distal tip of endoscopic end-effector 93 is known, the theta angle θ implicitly indicates the degree of rotation of the distal tip of endoscopic end-effector 93 about the axis of the spherical cap relative to an origin point along a periphery of plane 92, and the phi angle φ implicitly indicates the degree of separation between the distal tip of endoscopic end-effector 93 from the axis of the spherical cap.

A stage S72 of flowchart 70 encompasses a construction of a two-dimensional configuration space 100 of robot coordinate system 90 with respect to the possible ranges of the theta angle θ and the phi angle φ as defined by robot coordinate system 90. In particular, the configuration space construction involves a spherical projection of plane 92 of robot coordinate system 90 into a two-dimensional plane serving as configuration space 100. The resulting configuration space 100 represents a full configuration space of a tip of endoscopic end-effector 93 with respect to two settable parameters.

A stage S73 of flowchart 70 encompasses a pose determination of endoscopic end-effector 93 relative robotic coordinate system 90 involving a mapping of a robot vector in configuration space 100 based on a mapping of a tracking vector in image coordinate system 80. Specifically, motion of an image within the image coordinate system 80 over multiple digital video frames is mapped within configuration space 100. This mapping is qualitative with an unknown scale in view of the fact that a position in pixels (implicitly millimeters) within image coordinate system 80 is transferred to a pose of endoscopic end-effector 93 in two angles (radians) within robotic coordinate system 90 as represented by configuration space 100.

Figure 9:
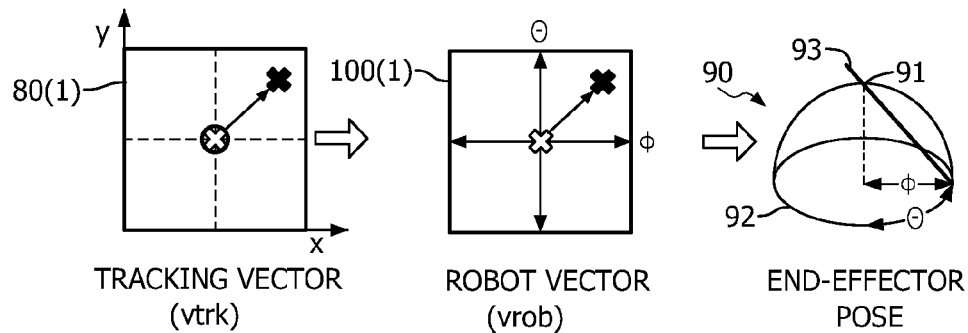
FIGS. 9-11 illustrate a first exemplary sequence of an end-effector pose determination in accordance with the flowcharts shown in FIG. 8.
Figure 10:
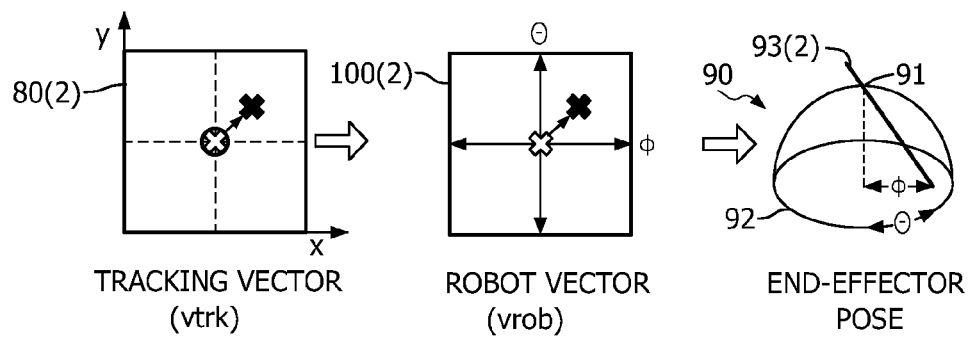
Figure 11:
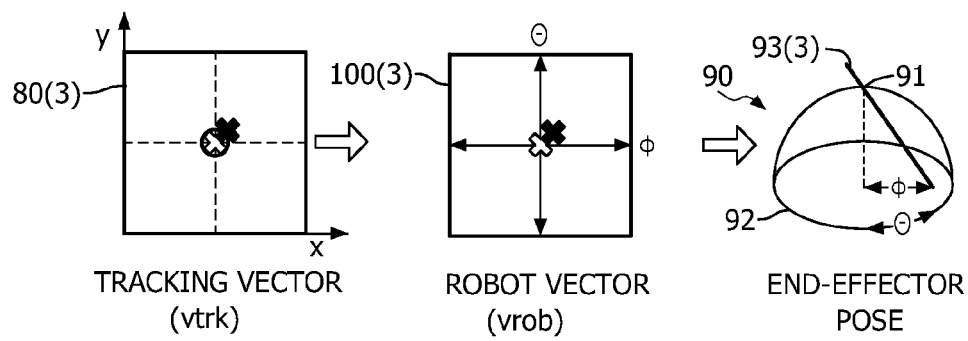

For example, as shown in FIGS. 9-11 over three (3) digital video frames, an identification of a tracking vector (vtrk) of a minimum magnitude as represented by the circle around the tracking point (white X) enables a mapping of the tracking vector (vtrk) as a robot vector (vrob) within configuration space 100. While the mapping scale is unknown, the position of the target point TG within image coordinate system 80 is transformed to a pose of endoscopic end-effector 93 in two angles (radians) within robotic coordinate system 90 as represented by configuration space 100. To this end, the tracking direction of tracking vector (vtrk) within image coordinate system 80 dictates a robotic direction of robot vector (vrob) within robotic coordinate system 90, which in turn is processed via inverse kinematics to move robotic joint(s) 41 to achieve the pose of endoscopic end-effector 93 within robotic coordinate system 90.

Figure 12:
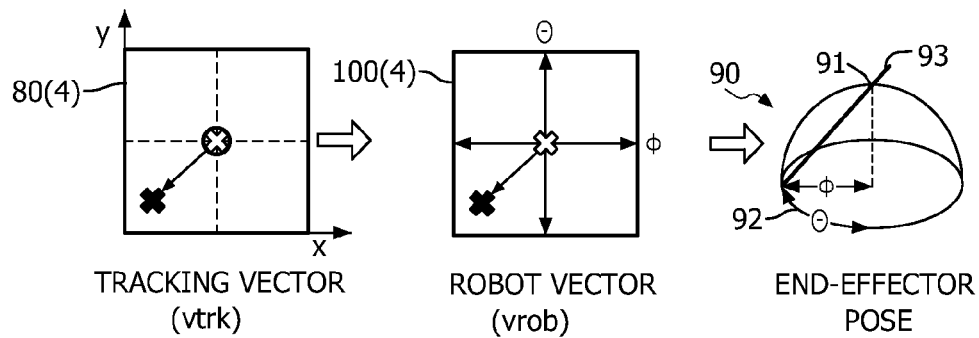
FIGS. 12-14 illustrate a second exemplary sequence of an end-effector pose determination in accordance with the flowcharts shown in FIG. 8.
Figure 13:
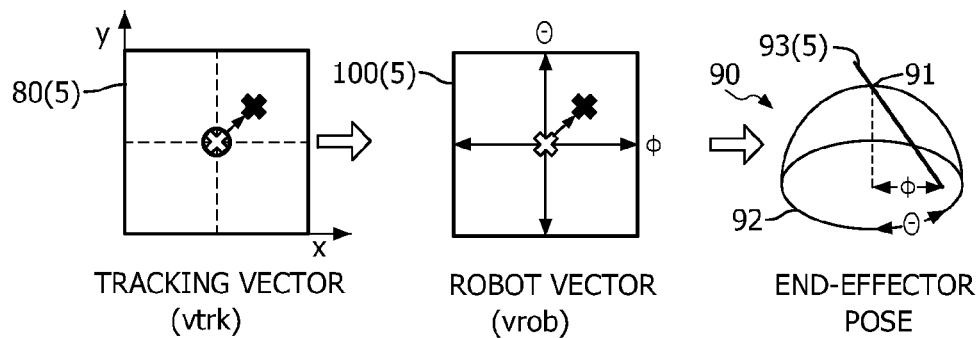
Figure 14:
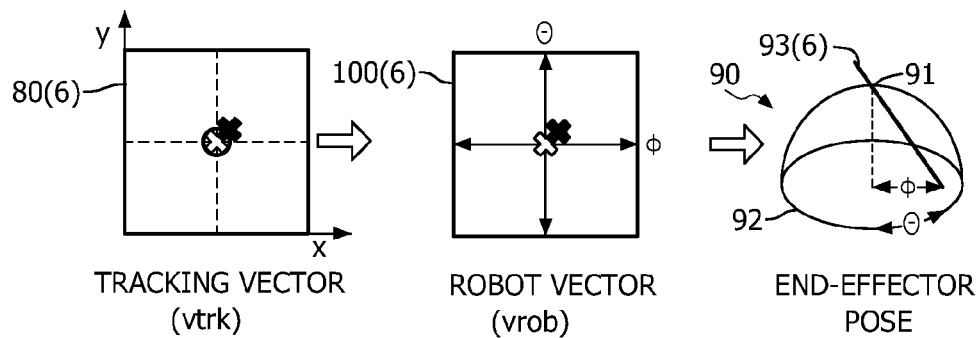

By further example, as shown in FIGS. 12-14 over three (3) digital video frames, again an identification of a tracking vector (vtrk) of a minimum magnitude enables a mapping of the tracking vector (vtrk) as a robot vector (vrob) within configuration space 100. Also again, while the mapping scale is unknown, the position of the target point TG within image coordinate system 80 is transformed into a pose of endoscopic end-effector 93 in two angles (radians) within robotic coordinate system 90 as represented by configuration space 100. To this end, the tracking direction of tracking vector (vtrk) within image coordinate system 80 dictates a robotic direction of robot vector (vrob) within robotic coordinate system 90, which in turn is processed via inverse kinematics to move the joint(s) 41 of robot 40 to achieve the pose of endoscopic end-effector 93 within robotic coordinate system 90.

Referring to FIGS. 9-14, as previously stated herein, the mapping scale between image coordinate system 80 and configuration space 100 is unknown. Thus, tracking vector (vtrk) is normalized (i.e., length set to one) and transferred as robot vector (vrob) to configuration space 100. The values of the theta angle θ and the phi angle φ associated with robot vector (vrob) therefore define a unit robot displacement in a given direction of robot vector (vrob). In practice, robot 40 may be velocity-controlled whereby the unit robot displacement is defined in radians/second in both the theta angle θ and the phi angle φ directions. Since robot vector (vrob) is normalized, velocities in the theta angle θ and the phi angle φ directions should be ≤1 radian/second. However, depending on other parameters (e.g., depth of feature in digital video frames 32, relative speed of the tracking point in digital video frames 32, etc.), the velocity of robot vector (vrob) may be insufficient for tracking point TR to reach target point TG, or may be too fast whereby tracking point TR overshoots the target point TG.

Figure 15:
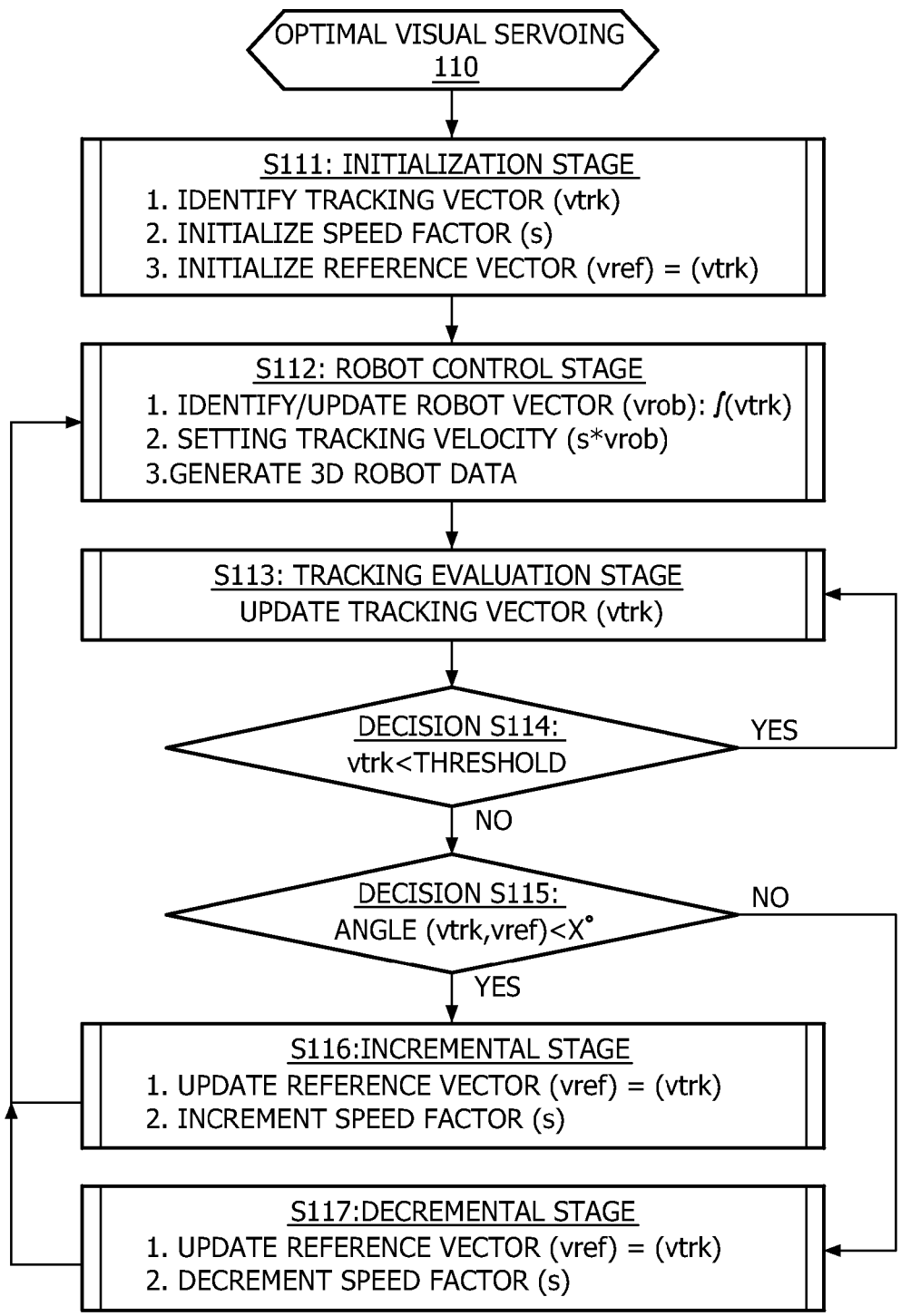
FIG. 15 illustrates a flowchart representative of a first exemplary embodiment of an optical visual servoing method in accordance with the present invention.
Figure 16:
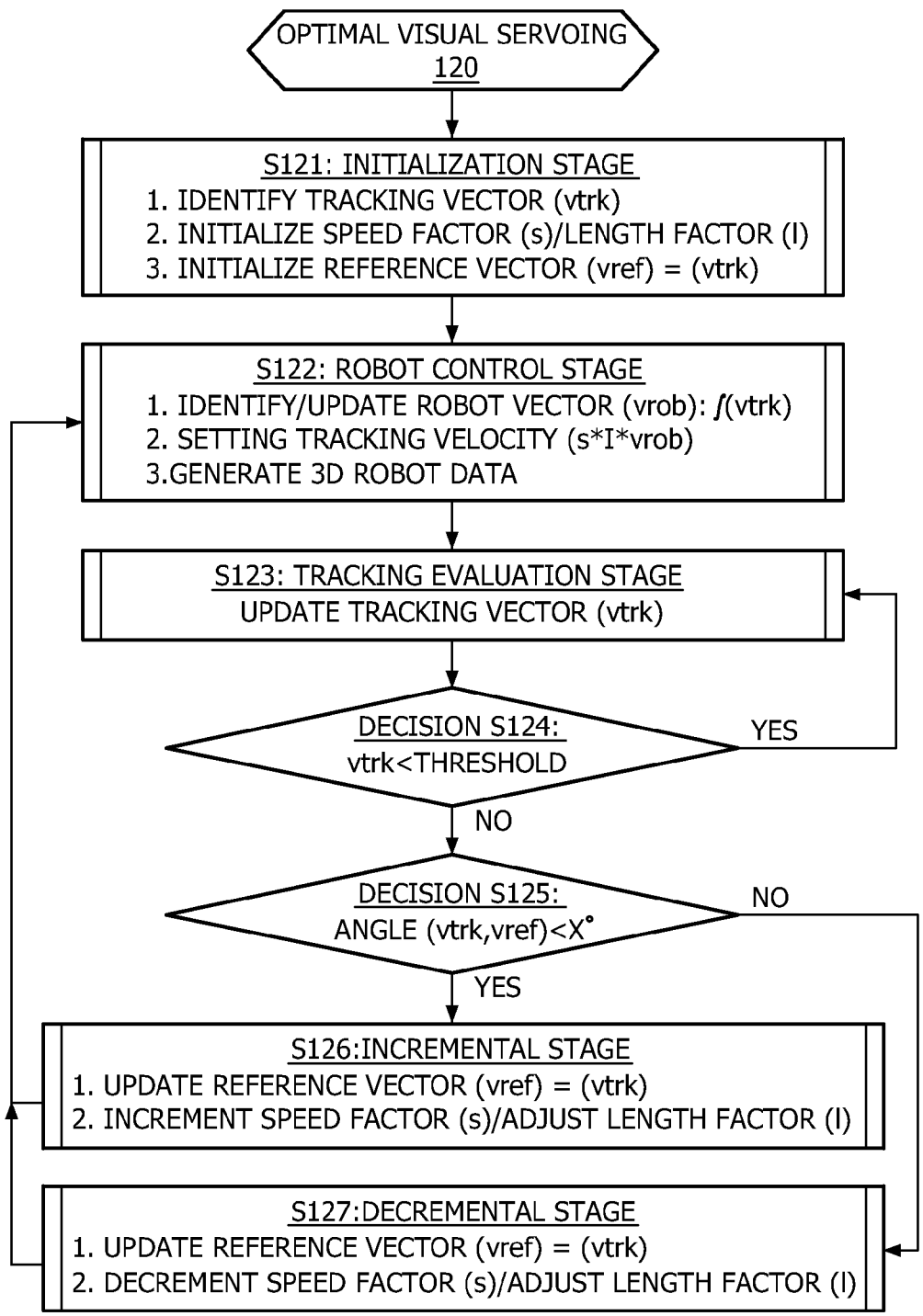
FIG. 16 illustrates a flowchart representative of a second exemplary embodiment of an optical visual servoing in accordance with the present invention.

To compensate for the unknown mapping scale between image coordinate system 80 and configuration space 100, FIG. 15 illustrates a flowchart 110 and FIG. 16 illustrates a flowchart 120 with both being representative of an optimal visual servoing method that may be implemented during stage S73 to optimize the tracking speed component of a tracking vector.

Referring to FIG. 15, stage S111 of flowchart 110 involves an initialization of a speed factor (s) and an identification of a tracking vector (vtrk) in image coordinate system 80 whenever the target point has been displaced from the tracking point between two (2) successive sampling frames of digital video frames 32. In practice, the initial value of speed factor (s) may be any dimensionless empirical value (e.g., ≤1≥). Stage S111 further involves an initialization of a reference vector (vref) equaling tracking vector (vtrk).

A stage S112 of flowchart 110 involves an identification of a robot vector (vrob) within configuration workspace 100 that involves a mapping of tracking vector (vtrk) within configuration workspace 100. Stage S112 further involves setting a tracking velocity as a product of speed factor (s) and robot vector (vrob) whereby speed factor (s) adjusts the radians/second value of the theta angle θ and the phi angle φ associated with robot vector (vrob). Tracking velocity (s*vrob) is mapped to robot coordinate space 100 to thereby use the corresponding theta angle θ and phi φ angle to generate 3D robot data as an indication of the robot movement needed for implementing tracking velocity (s*vrob).

As robot 40 is moved in accordance with the tracking velocity, any displacement between the tracking point and the target point must be updated from subsequent frames of digital video frames 32 in view of the facts that (1) the target point may be moving in image coordinate system 80 of successive sampling digital image frames 32 due to any movement of end-effector 42 and (2) the target point may be moving in a coordinate system of the environment. Stages S113-S117 of flowchart 110 are therefore utilized to adjust the tracking velocity at the sampling rate of digital video frames 32 (e.g., every frame of digital video frames 32 or at a specified frame-rate of digital video frames 32).

Specifically, stage S113 involves an updating of tracking vector (vtrk) between the tracking point and the target point in a successive sampling frame of digital video frames 32. Stage S114 determines whether tracking vector (vtrk) is less than an accuracy threshold that is established to maintain a stable positioning of robot 40 in the presence of insignificant noise within the successive sampling frame of digital video frames 32. If tracking vector (vtrk) is less than the accuracy threshold, then flowchart 110 returns to stage S113 to update tracking vector (vtrk) within the next successive sampling frame of digital video frames 32. Otherwise, flowchart 110 proceeds to stage S115 to determine if an angle between tracking vector (vtrk) and reference vector (vref) is less than an angular threshold X° (e.g., 90°).

If the angle between tracking vector (vtrk) and reference vector (vref) is less than the angular threshold X°, then flowchart 110 proceeds to stage S116 to update reference vector (vref) equal to the tracking vector (vtrk) and to increment speed factor (s), and thereafter returns to stage S112 to repeat the loop as needed for additional sampling frames of digital video frames 32. If the angle between tracking vector (vtrk) and reference vector (vref) is equal to or greater than the angular threshold X°, then flowchart 110 proceeds to stage S117 to update reference vector (vref) equal to the tracking vector (vtrk) and to decrement speed factor (s), and thereafter returns to stage S112 to repeat the loop as needed for additional sampling frames of digital video frames 32.

In practice, tracking vector (vtrk) and reference vector (vref) may change orientation if the user of system 20 rotates camera 30 (e.g., a rotation of an endoscope around its shaft or a rotation of a CCD camera at the proximal end of the endoscope). If that kind of motion is not allowed by the system, then stage S117 may be omitted.

The benefit of stages S113-S117 is the optimization of tracking velocity (s*vrob). Specifically, if the tracking point has moved between two sampling frames of digital video frames 32, stage S115 evaluates an angular displacement between a newly updated tracking vector (S113) and a previously updated reference vector (vref) to determine if the newly updated tracking vector (vtrk) is in the same general direction as the previously updated reference vector (vref) (e.g., angle (vtrk,vref)<90°) or if the newly updated tracking vector (vtrk) is pointing in a different direction as the previously updated reference vector (vref) (e.g., angle (e.g., (vtrk, vref))≤90°. In practice, the change of direction may be accomplished at any angle larger than 0° and smaller than 90°.

In the same general direction scenario, robot 40 is assumed to be moving in the correct direction for moving the tracking point in a direction of the target point in digital video frames 32 without having overshot the target point. In this case, the reference vector (vref) is updated and speed factor (s) is increased during stage S116 and the tracking of the target point continues during another loop of stages S112-S117. For example, as shown in FIG. 9, an initial tracking vector (vtrk) is identified within a first frame of image coordinate system 80(1) and utilized to map robot vector (vrob) in configuration workspace 100(1). Tracking velocity (s*vrob) is set for robot vector (vrob) whereby robot 40 is moved accordingly and tracking vector (vtrk) is updated within a second frame of image coordinate system 80(2) as shown in FIG. 10. Tracking vector (vtrk) of FIG. 10 is in the same general direction as tracking vector (vtrk) shown in FIG. 9. Thus, reference vector (vref) is updated as tracking vector (vtrk) shown in image coordinate system 80(1) and speed factor (s) is increased. In the subsequent loop of stages S112-S117, the updated tracking vector (vtrk) within the second frame of image coordinate system 80(2) is utilized to map robot vector (vrob) in configuration workspace 100(2). Tracking velocity (s*vrob) is then updated for robot vector (vrob) whereby robot 40 is moved accordingly and a new tracking vector (vtrk) is identified within a third frame of image coordinate system 80(3) as shown in FIG. 11. Tracking vector (vtrk) (not shown in FIG. 11) is less than the accuracy threshold of stage S114 as symbolized by the circle surrounding the tracking point and robot 40 is set in a fixed position until the next updated tracking vector (vtrk) is equal to or greater than the accuracy threshold.

In the different direction scenario, robot 40 is assumed to be moving in the correct direction for moving the tracking point in a direction of the target point in digital video frames 32 but overshoots the target point, or the target point has changed directions in a successive sampling frame of digital video frames 32. In this either case, reference vector (vref) is updated and speed factor (s) is decreased during stage S116 and the tracking of the target point continues during another loop of stages S112-S117. For example, as shown in FIG. 12, an initial tracking vector (vtrk) identified within a fourth frame of image coordinate system 80(4) is utilized to map robot vector (vrob) in configuration workspace 100(4). Tracking velocity (s*vrob) is generated for robot vector (vrob) whereby robot 40 is moved accordingly and a new tracking vector (vtrk) is identified within a fifth frame of image coordinate system 80(5) as shown in FIG. 13. Tracking vector (vtrk) of FIG. 13 is in a different direction as compared to the direction of the tracking vector (vtrk) shown in FIG. 12. Thus, reference vector (vref) is updated as tracking vector (vtrk) of image coordinate system 80(4) and speed factor (s) is decreased. In the subsequent loop of stages S112-S117, the updated tracking vector (vtrk) within the fifth frame of image coordinate system 80(5) is utilized to map robot vector (vrob) in configuration workspace 100(5). Tracking velocity (s*vrob) is then updated for robot vector (vrob) whereby robot 40 is moved accordingly and a new tracking vector (vtrk) is identified within a sixth frame of image coordinate system 80(6) as shown in FIG. 14. Tracking vector (vtrk) (not shown in FIG. 14) is less than the accuracy threshold of stage S114 as symbolized by the circle surrounding the tracking point and robot 40 is set in a fixed position until the next tracking vector (vtrk) is equal to or greater than the accuracy threshold.

Referring to FIG. 16, flowchart 120 is synonymous with flowchart 110 (FIG. 14) with the exception of an implementation of proportional control using a length factor (1) of the tracking vector in the image coordinate system 80. Length factor (1) is indicative of how far the tracking point is from the target point and may be expressed in pixels. Thus, length factor (1) is initialized accordingly during stage S121 of flowchart 120, and tracking velocity of robot vector (vrob) may be expressed as (s*l*vrob) in stage S122 of flowchart 120. In this case, the dimension of the speed factor (s) is mm/(s*pixel). In one embodiment, a proportional control of length factor (1) during stages 5126 and 5127 may enhanced with derivative and integral factors of the length factor (1), similar as in PID (proportional-integral-derivative) control known in art.

Figure 17:
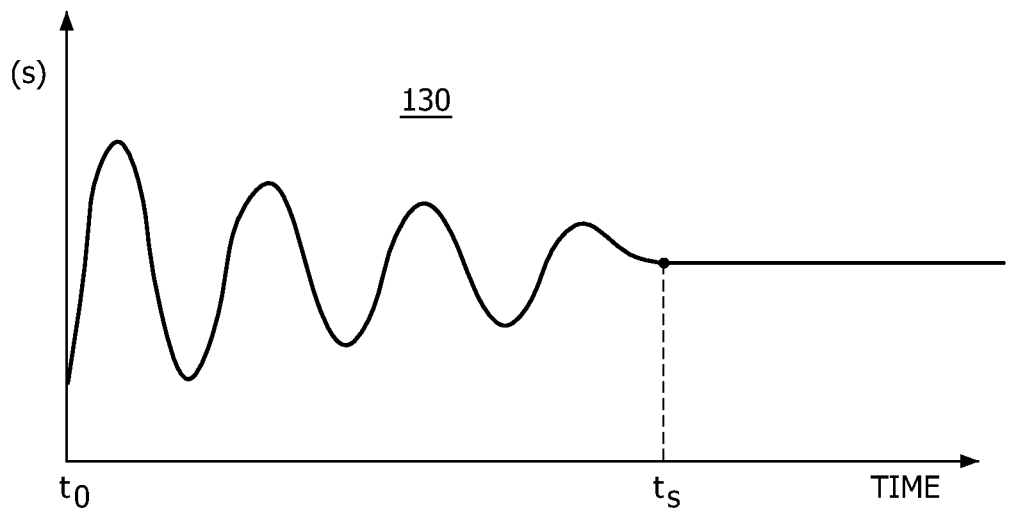
FIG. 17 illustrates an exemplary stabilization of a speed factor in accordance with the present invention.

FIGS. 9-14 illustrate two simple examples of an optimization of speed factor (s). In practice, an advantage of stages S112-S117 (FIG. 15) and stages S122-S127 (FIG. 16) is that visual servo 51 is learning an optimal speed factor (s) in real time. If the target point is moving with a constant velocity, an initial variation of speed factor (s) will stabilize after multiple frames of digital video frames 32 as shown in FIG. 17 with the stabilization of speed factor (s) after a time $t_s$ covering the frames. Otherwise, if the tracking point is moving with a varying velocity, an initial variation of speed factor (s) will stabilize after multiple frames of digital video frames 32 with some amount of noise.

Figure 18:
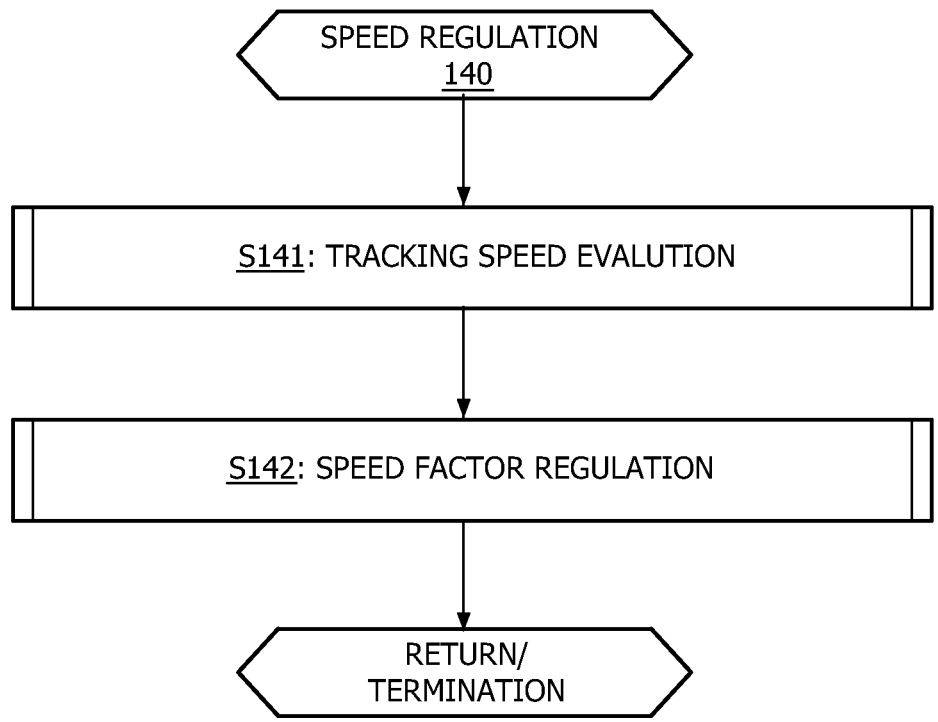
FIG. 18 illustrates a flowchart representative of an exemplary embodiment of a speed regulation method in accordance with the present invention.

In practice, the increment value and decrement value of speed factor (s) as shown in FIGS. 15 and 16 may be constant. Alternatively, FIG. 18 illustrates a flowchart 140 representative of a speed regulation method of the present invention. Specifically, a stage S141 of flowchart 140 encompasses an evaluation of the speed of the tracking velocity (s*rob) or (s*l*rob) in view of a tracking latency of the tracking point or in view of the application of system 20. In the tracking latency embodiment, the control of robot 40 is attempting to track the tracking point at its maximum speed of robot 40 possible at any given time. To this end, the stabilization of speed factor (s) and the tracking latency are evaluated for purposes of regulating speed factor (s) during a stage S142 of flowchart 140 in an attempt to track the tracking point at its maximum speed possible at any given time. For example, the increment value and the decrement value of speed factor (s) is decreased during stage S142 for a stable speed factor (s) having a low tracking latency or for an unstable speed factor (s) (e.g., target point overshoot tracking point). Conversely, the increment value and the decrement value of speed factor (s) are increased during stage S142 of flowchart 140 for a stable speed factor (s) having a high tracking latency. In practice, parameters affecting the tracking latency other than inherent robot speed includes, but is not limited to, distance between the tracking point and the target point, an insertion depth of camera 30, a distance between a tip of camera 30 and a RCM insertion point. Nonetheless, regulation of speed factor (s) maintains an optimization of tracking velocity (s*rob) or (s*1*vrob) despite any changes in the parameters.

In the application embodiment, the control of robot 40 is not attempting to track the tracking point within digital video frames 32 at a maximum speed of robot 40, but at a speed appropriate for the application. To this end, a speed range of tracking velocity (s*rob) or (s*1*vrob) is evaluated in view of a predicted motion of the tracking point determined by visual servo 51 from digital video frames 32 or supplied to visual servo 51 by an operator of system 20. Speed factor (s) is set accordingly during stage S142. For example, a static tracking of a surgical tool would ignore small tremors and speed factor (s) therefore would be set for ignoring small tremors. Also by example, a dynamic tracking of a beating heart involves fast changes in motion of the heart and speed factor (s) therefore would be set to follow the fast changes in the motion of the heart.

Figure 19:
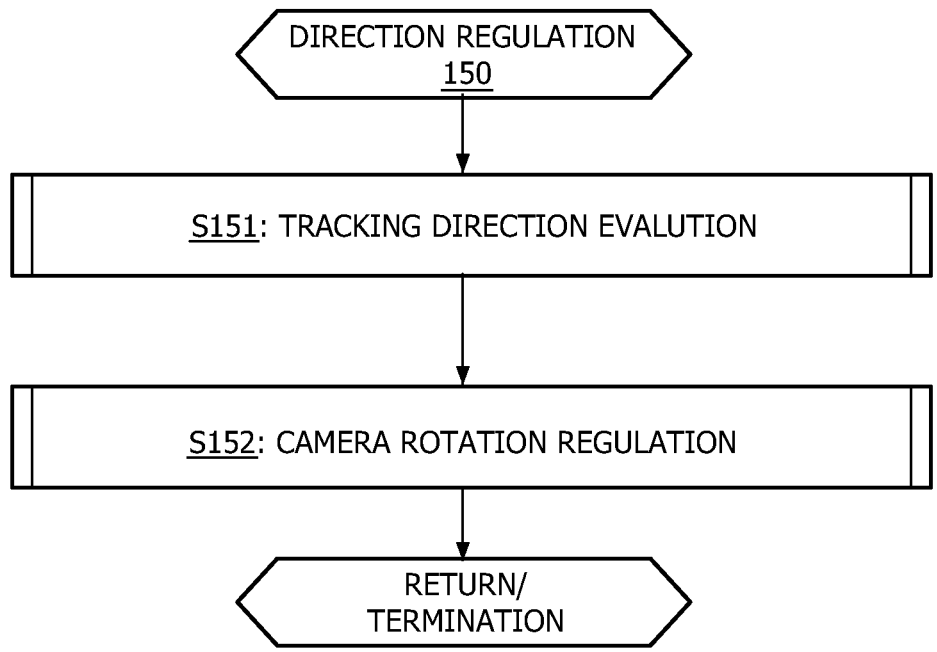
FIG. 19 illustrates a flowchart representative of an exemplary embodiment of a direction regulation method in accordance with the present invention.

Also in practice, the particular feature being tracked may be rotated relative to robot 40 (e.g., up-down and left-right movements are not the same in the two coordinate systems, particularly for a oblique optical viewing camera) and the control of robot 40 may oscillate around target point without ever reaching the target point. FIG. 19 illustrates a flowchart 150 representative of a direction evaluation of the present invention for correcting a potential oscillation of robot 40 around the target point. A stage S151 of flowchart 150 encompasses an evaluation of a tracking direction of tracking velocity (s*rob) or (s*1*vrob) involving a counting of a number of consecutive directions changes between two given frames of digital video frames 32. Upon the counter reaching a specified number of consecutive direction changes (preferably 2 or 3 consecutive direction changes), flowchart 150 proceeds to stage S152 to rotate the robot vector (vrob) as mapped in the configuration workspace 100 relative to tracking vector (vtrk) as mapped in the image coordinate system 80 prior to moving robot 40. The fastest technique for reaching convergence is to divide the configuration workspace into four (4) quadrants for rotation of 90°, 180° or 270°. Flowchart 150 is implemented during stage S112 whereby, upon detecting the correct quadrant, further divisions of the quadrant may be needed as the tracking direction is further evaluated.

Figure 20:
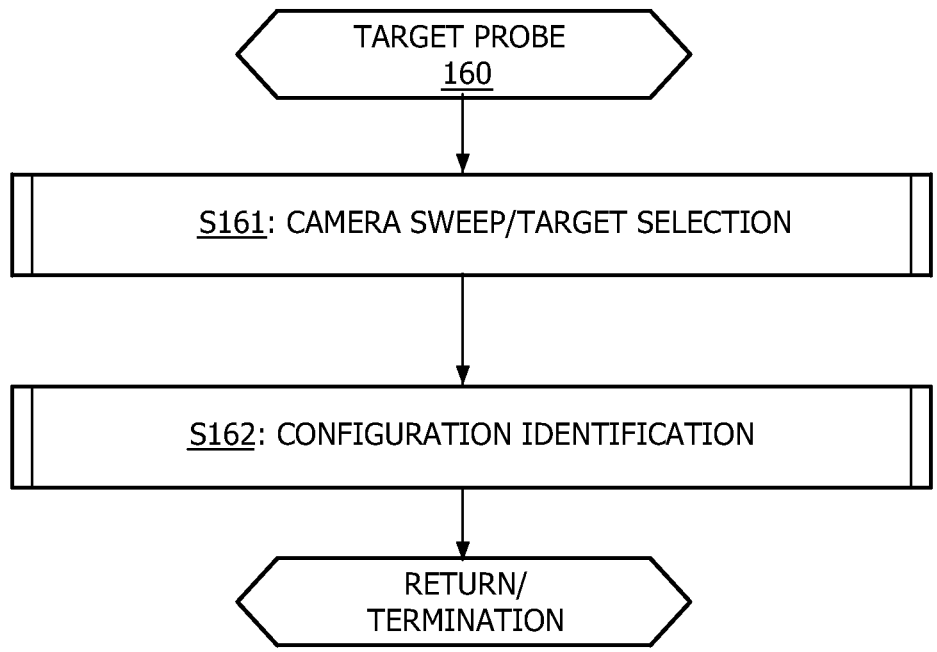
FIG. 20 illustrates a flowchart representative of an exemplary embodiment of a target probe method in accordance with the present invention.

Also in practice, robot 40 may be controlled to automatically find and track a particular feature within digital video frames 32 once an insertion point (e.g., a RCM point) has been defined for an oblique optical viewing camera 30. FIG. 20 illustrates a flowchart 160 representative of a target probe method for the automatic finding and tracking of a particular feature within image 40. A stage S161 of flowchart 160 encompasses a camera sweep involving a rotation of camera 30 about is axis relative to the insertion point. Once camera 30 has found the targeted feature, robot controller 50 locks the configuration of the sweep during a stage S162 of flowchart 160 as the robot coordinate system 90 for purposes of direction setting as previously described herein.

Although the present invention has been described with reference to exemplary aspects, features and implementations, the disclosed systems and methods are not limited to such exemplary aspects, features and/or implementations. Rather, as will be readily apparent to persons skilled in the art from the description provided herein, the disclosed systems and methods are susceptible to modifications, alterations and enhancements without departing from the spirit or scope of the present invention. Accordingly, the present invention expressly encompasses such modification, alterations and enhancements within the scope hereof.

The invention claimed is:

1. A robotic system (20), comprising:
 a camera (30) having an optical view for acquiring a sequence of digital video frames (32) illustrating an image;
 a robot (40) including an end-effector (42) and at least one robotic joint (41) for maneuvering the end-effector (42); and
 a robot controller (50) in communication with the camera (30) and the robot (40), the robot controller (50) including a visual servo (51) for controlling a pose of the end-effector (42) relative to an image feature within each digital video frame (32),
 wherein, for each digital video frame (32), the visual servo (51) is operable to identify a tracking vector (vtrk) within an image coordinate system (80) of the digital video frame (32) extending from a tracking point (TR) to a target point (TG) associated with the image feature, to map the tracking vector (vtrk) within a configuration space (100) constructed from a robotic coordinate system (90) associated with the end-effector (42), and to derive a pose of the end-effector (42) within the robotic coordinate system (90) from the mapping of the tracking vector (vtrk) within the configuration space (100).

2. The robotic system (20) of claim 1, wherein the camera (30) is an endoscope mounted to the end-effector (42).

3. The robotic system (20) of claim 1, wherein the visual servo (51) is further operable to track any movement of the image feature within the digital video frames (32).

4. The robotic system (20) of claim 1, wherein the visual servo (51) is further operable to command at least one robotic joint movement for at least one derived pose of the end-effector (42).

5. The robotic system (20) of claim 1, wherein an identification of a tracking vector (vtrk) sets a tracking velocity including a tracking direction and a tracking speed of the tracking vector (vtrk) within the image coordinate system (80).

6. The robotic system (20) of claim 5, wherein the tracking direction of the tracking vector (vtrk) as currently mapped in the configuration space (100) is rotated between at least two quadrants of the configuration space (100) in response to a specified number of consecutive direction changes between at least two tracking vectors (vtrk) previously mapped in the configuration space (100).

7. The robotic system (20) of claim 5, wherein a tracking speed of the tracking vector (vtrk) as mapped in the configuration space (100) is adjusted by a speed factor (s) responsive to a degree of movement of the image feature of successive sampling frames of the digital video frames (32).

8. The robotic system (20) of claim 7, wherein the speed factor (s) is a function of at least one of a tracking latency of the tracking vector (vtrk) and a speed corresponding for an application of the robotic system (20).

9. The robotic system (20) of claim 5, wherein a tracking speed of the tracking vector (vtrk) as mapped in the configuration space (100) is adjusted by a length factor (1) responsive to a distance between the tracking point (TR) and the target point (TG).

10. The robotic system (20) of claim 9, wherein the length factor (1) is a function of at least one of a proportional control, an integral control and a derivative control.

11. The robotic system (20) of claim 1, wherein the robotic configuration space (90) represents a rotation of the camera (30) about an axis relative to a remote center of rotation.

12. The robotic system (20) of claim 11, wherein the robotic configuration space (90) is established by a probe and an identification of the image feature as the camera (30) is rotated about the axis relative to a remote center of rotation.

13. A visual servo (51) for a camera (30) having an optical view and a robot (40) having an end-effector (42) and at least one joint (41) for maneuvering end-effector (42), the visual servo (51) comprising:
a feature tracking module for tracking any movement of the image feature within the digital video frames (32); and
a direction setting module responsive to the feature tracking module for identifying a tracking vector within an image coordinate system of the digital video frame extending from a tracking point to a target point associated with the image feature, mapping the tracking vector within a configuration space constructed from a robotic coordinate system associated with the end-effector, and deriving a pose of the end-effector within the robotic coordinate system from the mapping of the tracking vector within the configuration space.

14. The visual servo (51) of claim 13, further comprising:
an inverse kinematics module responsive to the direction setting module for commanding at least one robotic joint movement (43) for at least one derived pose of the end-effector (42).

15. The visual servo (51) of claim 13, wherein the camera (30) is an endoscope mounted on the end-effector (42).

16. A robotic control method including a camera (30) having an optical view and a robot (40) having an end-effector (42) and at least one joint (41) for maneuvering end-effector (42), the robotic control method comprising:
acquiring a sequence of digital video frames (32) illustrating an image as optically viewed by the camera (30); and
executing a visual servoing for controlling a pose of end-effector (42) relative to an image feature within each digital video frame (32), wherein the visual servoing for each digital video frame includes:
identifying a tracking vector within an image coordinate system of the digital video frame extending from a tracking point to a target point associated with the image feature,
mapping the tracking vector within a configuration space constructed from a robotic coordinate system associated with the end-effector, and
deriving a pose of the end-effector within the robotic coordinate system from the mapping of the tracking vector within the configuration space.

17. The robotic control method of claim 16, further comprising:
tracking any movement of the image feature within the digital video frames (32).

18. The robotic control method of claim 16, further comprising:
commanding at least one robotic joint movement for at least one derived pose of the end-effector (42).

19. The robotic control method of claim 16, wherein an identification of a tracking vector (vtrk) sets a tracking velocity including a tracking direction and a tracking speed of the tracking vector (vtrk) within the image coordinate system (80).

20. The robotic system (20) of claim 16, wherein the robotic configuration space (90) represents a rotation of the camera (30) about an axis relative to a remote center of rotation.

\* \* \* \* \*